(12) United States Patent
Xu et al.

(10) Patent No.: US 11,938,466 B2
(45) Date of Patent: Mar. 26, 2024

(54) CATALYST SYSTEMS AND METHODS OF SYNTHESIZING CATALYST SYSTEMS

(71) Applicant: King Abdullah University of Science and Technology, Thuwal (SA)

(72) Inventors: Leilei Xu, Thuwal (SA); Jean-Marie Basset, Thuwal (SA); Pradeep Kumar Doggali, Thuwal (SA)

(73) Assignee: King Abdullah University of Science and Technology, Thuwal (SA)

(*) Notice: Subject to any disclaimer, the term of this patent is extended or adjusted under 35 U.S.C. 154(b) by 26 days.

(21) Appl. No.: 17/315,886

(22) Filed: May 10, 2021

(65) Prior Publication Data
US 2022/0355278 A1   Nov. 10, 2022

(51) Int. Cl.
| | | |
|---|---|---|
| B01J 29/40 | (2006.01) |
| B01J 21/02 | (2006.01) |
| B01J 21/06 | (2006.01) |
| B01J 35/00 | (2006.01) |
| B01J 35/10 | (2006.01) |
| B01J 37/04 | (2006.01) |
| B01J 37/06 | (2006.01) |
| B01J 37/08 | (2006.01) |
| C10G 47/02 | (2006.01) |

(52) U.S. Cl.
CPC ............ B01J 29/40 (2013.01); B01J 21/02 (2013.01); B01J 21/06 (2013.01); B01J 35/0006 (2013.01); B01J 35/1019 (2013.01); B01J 35/1023 (2013.01); B01J 35/1038 (2013.01); B01J 35/1042 (2013.01); B01J 35/1061 (2013.01); B01J 37/04 (2013.01); B01J 37/06 (2013.01); B01J 37/08 (2013.01); C10G 47/02 (2013.01); C10G 2400/20 (2013.01)

(58) Field of Classification Search
None
See application file for complete search history.

(56) References Cited

FOREIGN PATENT DOCUMENTS

WO    2019035045 A1    2/2019

OTHER PUBLICATIONS

Firmansyah et al., Synthesis and characterization of fibrous silica ZSM-5 for cumene hydrocracking, Catal. Sci. Technol., 2016 (Year: 2016).*
Researchgate, What is the difference between average pore diameter by BET and BJH? https://www.researchgate.net/post/What-is-the-difference-between-average-pore-diameter-by-BET-and-BJH/54b385a4d039b1af148b45a1/citation/download (Year: 2015).*
Polshettiwar et al., High-surface-area silica nanospheres (KCC-1) with a fibrous morphology, Angew. Chem. Int. Ed., 2010, 49, 9652-9656 (Year: 2010).*

(Continued)

Primary Examiner — Coris Fung
Assistant Examiner — Keling Zhang
(74) Attorney, Agent, or Firm — DINSMORE & SHOHL LLP

(57) ABSTRACT

Embodiments of catalyst systems and methods of synthesizing catalyst systems are provided. The catalyst system may include a core comprising a zeolite; and a shell comprising a microporous fibrous silica. The shell may be in direct contact with at least a majority of an outer surface of the core. The catalyst system may have a Si/Al molar ratio greater than 5. At least a portion of the shell may have a thickness of from 50 nanometers (nm) to 360 nm.

16 Claims, 12 Drawing Sheets

(56) References Cited

OTHER PUBLICATIONS

Berrichi et al., Ga doped SBA-15 as an active and stable catalyst for Friedel-Crafts liquid phase acylation, Applied Catalysis A: General 298, 2006 (Year: 2006).*
Akah et al., "Maximizing propylene production via FCC technology", Appl Petrochem Res, DOI 10.1007/s13203-015-0104-3, Mar. 4, 2015.
Alamri et al., "Self-cleaning superhydrophobic epoxy coating based on fibrous silica-coated iron oxide magnetic nanoparticles", Journal of Colloid and Interface Science, vol. 513, pp. 349-356, 2018.
Atabaev et al., "Mesoporous silica with fibrous morphology: A multifunctional core-shell platform for biomedical applications", Nanotechnology, vol. 24, 345603 (7pp), 2013.
Aziz et al., "Controllable structure of fibrous SiO2—ZSM-5 support decorated with TiO2 catalysts for enhanced photodegradation of paracetamol", Applied Surface Science, vol. 455, pp. 84-95, 2018.
Barzetti et al., "Pyridine and ammonia as probes for FTIR analysis of solid acid catalysts", J. Chem. Soc., Faraday Trans., vol. 92, No. 8, pp. 1401-1407, 1996.
Choi et al., "A facile approach for preparation of tunable acid nano-catalysts with hierarchically mesoporous structure", The Royal Society of Chemistry, DOI: 10.1039/c0xx00000x, 2014.
Chong et al., "Dry reforming of methane over Ni/dendritic fibrous SBA-15 (Ni/DFSBA-15): Optimization, mechanism, and regeneration studies", International Journal of Hydrogen Energy, vol. 45, pp. 8507-8525, 2020.
Chong et al., "Facile synthesis of tunable dendritic fibrous SBA-15 (SFSBA-15) with radial wrinkle structure", Microporous and Mesoporous Materials, vol. 294, 109872, 2020.
Fauzi et al., "Altering fiber density of cockscomb-like fibrous silica-titania catalysts for enhanced photodegradation of ibuprofen", Journal of Environmental Management, vol. 227, pp. 34-43, 2018.
Firmansyah et al., "Synthesis and characterization of fibrous silica ZSM-5 for cumene hydrocracking", Catalysis Science and Technology, vol. 6, 5178-5182, 2016.
Firmansyah et al., "Supplementary Information—Synthesis and characterization of fibrous silica ZSM-5 for cumene hydrocracking", Catalysis Science and Technology, vol. 6, 5178-5182, 2016.
Ghani et al., "Tailored mesoporosity and acidity of shape-selective fibrous silica beta zeolite for enhanced toluene co-reaction with methanol", Chemical Engineering Science, vol. 193, pp. 217-229, 2019.
Hambali et al., "Unique structure of fibrous ZSM-5 catalyst expedited prolonged hydrogen atom restoration for selective production of propylene from methanol", International Journal of Hydrogen Energy, https://doi.org/10.1016/j.jhydene.2019.11.236, Nov. 19, 2019.
Hussain et al., "New insights on the effect of the H2/Co ratio for enhancement of CO methanation over metal-free fibrous silica ZSM-5: Thermodynamic and mechanistic studies", Energy Conversion and Management, vol. 199, 112056, 2019.
Hyde, "Light olefins market review", Foro Pemex Petroquimica, Mexico 2012.
Ibrahim et al., "Enhanced n-hexane hydroisomerization over bicontinuous lamellar silica mordenite supported platinum (Pt/HM@KCC-1) catalyst", International Journal of Hydrogen Energy, vol. 45, pp. 18587-18599, 2020.
Izan et al., "Additional Lewis acid sites of protonated fibrous silica@BEA zeolite (HSi@BEA) improving the generation of protonic acid sites in the isomerization of C6 alkane and cycloalkanes", Applied Catalysis A, General, vol. 570, pp. 228-237, 2019.
Jung et al., "Effect of copper surface area and acidic sites to intrinsic catalytic activity for dimethyl ether synthesis from biomass-derived syngas", Applied Catalysis B: Environmental, vol. 126, pp. 1-8, 2012.
Le et al., "Palladium nanoparticles immobilized on core-shell magnetic fibrous as highly efficient and recyclable heterogeneous catalyst for reduction of 4-nitrophenol and Suzuki coupling reactions", Journal of Materials Chemistry A, vol. 2, No. 46, pp. 19696-19706, 2014.
Ma et al., "The influence of straight pore blockage on the selectivity of methanol to aromatics in nanosized Zn/ZSM-5: an atomic Cs-corrected STEM analysis study", RSC advances, vol. 6, No. 78, pp. 74797-74801, 2016.
Park et al., "IR study on methanol-to-olefin reaction over zeolites with different pore structures and acidities", Applied Catalysis A: General, vol. 356, pp. 180-188, 2009.
Peng et al., "One-Pot synthesis of benzamide over a robust tandem catalyst based on center radially fibrous silica encapsulated TS-1", The Royal Society of Chemistry, vol. 49, pp. 2709-2711, 2013.
Peng et al., "One-pot synthesis of primary amides on bifunctional Rh(OH)x/TS-1@KCC-1 catalysts", Chinese Journal of Catalysis, vol. 34, pp. 2057-2065, 2013.
Prasad et al., "Single-step synthesis of DME from syngas on Cu—ZnO-Al2O3/zeolite bifunctional catalysts: The superority of ferrierite over the other zeolites", Fuel Processing Technology, vol. 89, pp. 1281-1286, 2008.
Qian et al., "Supplemental Information: Controllable fabrication of uniform core-shell structured zeolite@SBA-15 composites", The Royal Society of Chemistry, 2011.
Qu et al., "Silica Microspheres with Fibrous Shells: Synthesis and Application in HPLC", Analytical Chemistry, vol. 87, pp. 9631-9638, Aug. 30, 2015.
Radhakrishnan et al., "A hybrid magnetic core-shell fibrous silica nanocomposite for a chemosensor-based highly effective fluorescent detection of Cu(II)", Royal Chemistry of Chemistry, vol. 7, pp. 45824-45833, 2017.
Rostamizadeh et al., "Bifunctional and bimetallic Fe/ZSM-5 nanocatalysts for methanol to olefin reaction", Fuel, vol. 181, pp. 537-546, 2016.
Sun et al., "A multifunctional magnetic core-shell fibrous silica sensing probe for highly sensitive detection and removal of Zn2+ from aqueous solution", Royal Society of Chemistry, Journal of Material Chemistry C, vol. 3, pp. 4713-4722, 2015.
Teh et al., "Fibrous silica mesoporous ZSM-5 for carbon monoxide methanation", Applied Catalysis A: General, vol. 523, pp. 200-208, 2016.
Yang et al., "Enhanced aromatic selectivity by the sheet-like ZSM-5 in syngas conversion", Journal of Energy Chemistry, vol. 35, pp. 44-48, 2019.
Yu et al., "Synthesis of fibrous monodisperse core-shell Fe3O4/SiO2/KCC-1", Materials Letters, vol. 106, pp. 151-154, 2013.
Ishihara, "Preparation and reactivity of hierarchical catalysts in catalytic cracking", Fuel Processing Technology, vol. 194, 37 pages, 2019.
Saudi Arabia Office Action pertaining to Application No. 122431044 dated Mar. 23, 2023, 9 pages.

* cited by examiner

CATALYST SYSTEMS AND METHODS OF SYNTHESIZING CATALYST SYSTEMS

TECHNICAL FIELD

Embodiments of the present disclosure generally relate to catalyst systems and more specifically relate to catalyst systems for the processing of petroleum based feeds.

BACKGROUND

In recent years, the demand for light olefins, including ethylene and propylene, has increased dramatically to feed the growing markets for polypropylene, polyethylene, propylene oxide and acrylic acid. Currently, most of the propylene produced worldwide is a by-product from steam cracking and Fluid Catalytic Cracking (FCC) of naphtha. Additionally, olefin metathesis is considered to be a useful reaction to shift the composition of a pool of low-value butenes to meet market demand for propylene.

SUMMARY

The catalytic cracking of crude oil to produce light olefins has been receiving more attention in the petroleum industries, and great efforts have been devoted to maximizing the selectivity of light olefins during catalytic cracking processes. Attempts to maximize selectivity involve integrating additional functionalities (such as pre-cracking, desulfurization, and denitrogenation) into zeolite-based catalysts.

Accordingly, ongoing needs exist for catalyst systems, which allow for the selective production of light olefins by integrating additional functionalities (such as pre-cracking, desulfurization, and denitrogenation) into zeolite-based catalysts.

To address these needs, catalyst systems and methods of synthesizing catalyst systems are disclosed, which include a core-shell morphology and where the shell includes a mesoporous fibrous silica. The zeolite core may provide catalytic sites for cracking functionalities, and the mesoporous fibrous silica shell may provide catalytic sites for one or more additional functionalities, such as pre-cracking, desulfurization, demetalization, and denitrogenation functionalities. Additionally, the core-shell structure itself may enable the spatial separation of these different types of catalytic active sites and their utilization in a sequential manner. The shell may be composed of acidic sites that can be used to pre-crack the crude oil large molecules or trap metals in crude oil feedstock. The pre-cracking fragments that pass through the shell can then easily diffuse into the micropores of the zeolite core, where they can be further cracked into smaller molecules. Additionally or alternatively, the crude oil feedstock may undergo desulfurization and denitrogenation over the corresponding catalytic active sites of the shell before the final cracking takes place at the acid sites in the zeolite core. For example, when utilizing the disclosed catalyst systems in catalytic cracking processes, the crude oil feedstock may undergo desulfurization and denitrogenation over the corresponding catalytic active sites of the shell before a cracking step takes place at the acid sites in the zeolite core.

According to one or more embodiments, catalyst systems are provided. Embodiments of the catalyst system may include a core comprising a zeolite and a shell comprising a microporous fibrous silica. The shell may be in direct contact with at least a majority of an outer surface of the core. The catalyst system may have a Si/Al molar ratio greater than 5. At least a portion of the shell may have a thickness of from 50 nanometers (nm) to 360 nm.

According to one or more embodiments, a method for converting hydrocarbons is provided. The method may include contacting a feed with a catalyst system comprising a core and a shell. The core may comprise a zeolite. The shell may comprise a microporous fibrous silica. The shell may be in direct contact with at least a majority of an outer surface of the core. The catalyst system may have a Si/Al molar ratio greater than 5. At least a portion of the shell may have a thickness of from 50 nanometers (nm) to 360 nm. The shell may pre-crack the feed to produce a pre-cracked feed, and the core may crack the feed to produce light olefins. In embodiments, the feed may be crude oil.

Additional features and advantages of the present embodiments will be set forth in the detailed description which follows, and in part will be readily apparent to those skilled in the art from that description or recognized by practicing the described embodiments, including the detailed description which follows, the claims, as well as the appended drawings.

DETAILED DESCRIPTION

Embodiments of the present disclosure are directed to catalyst systems, methods of synthesizing catalyst systems, and methods for utilizing catalyst systems.

As stated previously, embodiments of the catalyst systems described herein may have a core-shell morphology. Without being bound by theory, the core-shell morphology of the catalyst systems may provide additional functionalities (such as pre-cracking, desulfurization, demetallization, and denitrogenation functionalities) as compared to zeolite-based catalysts that do not have a core-shell morphology. For example, when utilized in crude oil catalytic cracking processes, the shell of the core-shell morphology may facilitate the purification or pretreatment of crude oil feedstock.

The catalyst systems and processes described are applicable for a wide variety of heavy oil feeds, including crude oils, vacuum residue, tar sands, bitumen and vacuum gas oils using a catalytic hydrotreating pretreatment process. As used herein, "crude oil" may refer to a feedstock having an American Petroleum Institute (API) gravity of from 25 degrees to 50 degrees. For example, the heavy oil feed utilized may be Arab Heavy crude oil. The typical properties for an Arab Heavy crude oil are shown in Table 1.

TABLE A

Arab Heavy Export Feedstock.

| Analysis | Units | Value |
| --- | --- | --- |
| American Petroleum Institute (API) gravity | degree | 27 |
| Density | grams per cubic centimeter (g/cm$^3$) | 0.8904 |
| Sulfur Content | Weight percent (wt. %) | 2.83 |
| Nickel | Parts per million by weight (ppmw) | 16.4 |
| Vanadium | ppmw | 56.4 |
| NaCl Content | ppmw | <5 |
| Conradson Carbon Residue (CCR) | wt. % | 8.2 |
| C5 Asphaltenes | wt. % | 7.8 |
| C7 Asphaltenes | wt. % | 4.2 |

Once the crude oil has traveled through and been pretreated by the shell, it may contact the acidic sites of core within the catalyst system, where the pretreated crude oil is subsequently cracked. Accordingly, the pre-cracking functionalities provided by the shell may allow for improved cracking functionalities provided by the core. Together, the core and the shell therefore allow for an improved overall yield of light olefins and other products.

Figure 1:
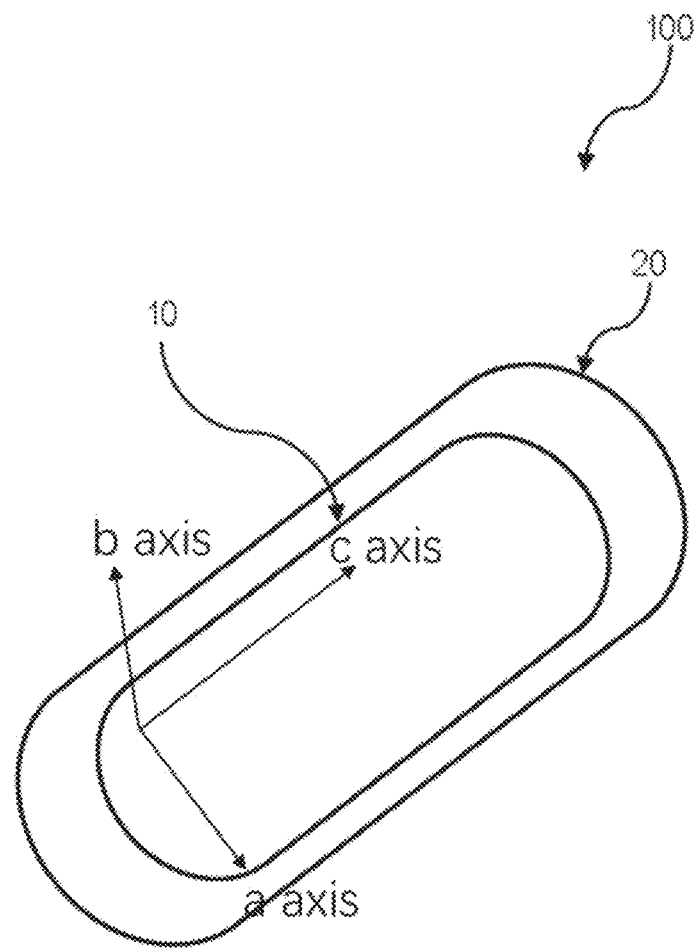
FIG. 1 depicts a catalyst system, in accordance with one or more embodiments described herein.

Embodiments of catalyst systems will now be described. Referring now to FIG. 1, the catalyst system 100 may have a core-shell type morphology, which includes a core 10 and shell 20. The core 10 may comprise a core material. The shell 20 may comprise a shell material. In embodiments, the shell 20 may surround at least a portion of the outer surface of the core 10. In further embodiments, the shell 20 may entirely surround the outer surface of the core 10. In embodiments, the core 10, comprising the core material, may be prepared separately from the shell 20. As described subsequently in more detail, in such embodiments, the shell material may then be synthesized to form a shell 20 around the prepared core 10.

The core material may include a zeolite. The zeolitic core may provide the cracking functionality as previously described. In embodiments, the zeolite may be a ZSM-5 zeolite, a TS-1 zeolite, a beta zeolite, or a Y zeolite, and other zeolites known in the art. In further embodiments, the core material comprises a ZSM-5 zeolite.

A ZSM-5 zeolite is an aluminosilicate zeolite of a mordenite framework inverted (MFI) developed by Mobil and belonging to the pentasil family of zeolites, so called owing to rings of five silicon atoms prevalent in the zeolite framework. ZSM-5 has a nominal chemical formula of $Na_nAl_nSi_{96-n}O_{192} \cdot 16H_2O$, where subscript n is from 0 to 27. The subscript n in the ZSM-5 thus indicates a silica-to-alumina ratio (SAR) of the zeolite. ZSM-5 zeolites may be produced having silica-to-alumina molar ratios (Si/Al molar ratio) as small as 12 and as large as approaching infinity if nearly all of the aluminum atoms are replaced by silicon. In embodiments, the ZSM-5 may have a Si/Al molar ratio of from 12 to 60, from 12 to 40, from 12 to 20, from 20 to 60, from 20 to 40, or from 40 to 60. The sodium ions in ZSM-5, of equal number to the number of aluminum atoms, maintain neutral charge in the zeolite.

The ZSM-5 may also be defined by porosity. A micropore volume represents the specific volume corresponding to the microporous structure of ZSM-5. The pore size ranges for micropores are in conformity with conventionally understood size ranges for such pore classifications with micropores representing pores under 2 nanometers (nm) in diameter. A total pore volume would additionally include any mesopores and macropores, if present. In embodiments, the average pore size of the ZSM-5 is from 0.5 nm to 50 nm, from 0.5 nm to 40 nm, from 0.5 nm to 30 nm, from 0.5 nm to 20 nm, from 0.5 nm to 10 nm, from 10 nm to 50 nm, from 10 nm to 40 nm, from 10 nm to 30 nm, from 10 nm to 20 nm, from 20 nm to 50 nm, from 20 nm to 40 nm, from 20 nm to 30 nm, from 30 nm to 50 nm, from 30 nm to 40 nm, or from 40 nm to 50 nm.

In one or more embodiments, the ZSM-5 may have a surface area defined by a Brunauer-Emmett-Teller (BET) analysis ($S_{BET}$) of at least 300 square meters per gram (m$^2$/g), a $S_{BET}$ surface area of at least 325 m$^2$/g, or a $S_{BET}$ surface area of at least 350 m$^2$/g. In one or more embodiments, the ZSM-5 zeolite catalyst is a commercially available ZSM-5. For example, the ZSM-5 may be CBV3024E from Zeolyst International (Conshohocken, Pennsylvania, USA). Without being bound by theory, the surface area of the pores of the ZSM-5 may individually affect the butenes cracking reaction when utilized in a cracking unit. An increased surface area provides increased interaction between the individual catalyst components and the constituents of the crude oil passed into the core thereby allowing for increased conversion activity.

In embodiments, the core 10 may have a thickness along its b axis of from 110 nanometers (nm) to 140 nm, from 110 nm to 130 nm, from 110 nm to 120 nm, from 120 nm to 140 nm, from 120 nm to 130 nm, or from 130 nm to 140 nm.

Embodiments of the shell 20 will now be described. As stated previously, the shell 20 may accommodate one or more of pre-cracking, desulfurization, and denitrogenation functionalities. The functionalities of the shell 20 may allow for enhanced cracking within the core 10.

The shell material of the catalyst system 100 described herein may include a mesoporous, fibrous silica. As used herein a "mesoporous fibrous silica" refers to a zeolite having fibers that are porous in nature or a zeolite having channel-like mesopores. In embodiments, mesoporous fibrous silica may have mesopores with an average pore size of from 2 to 50 nm. The presently disclosed mesoporous fibrous silicas may have an average pore size of greater than 2 nm, such as from 4 nm to 16 nm, from 6 nm to 14 nm, from 8 nm to 12 nm, or from 9 nm to 11 nm. In some embodiments, the majority of the mesopores may be greater than 8 nm, greater than 9 nm, or even greater than 10 nm. The mesopores of the mesoporous fibrous silicas described may range from 2 nm to 40 nm, and the median pore size may be from 8 to 12 nm. Without being bound by theory, bulky substrate molecules of crude oil (including, for example, 1,3,5-triisopropylbenzene, naphtalenes, naptha, kerosene, and substituted aromatics) may diffuse faster and more easily into the mesoporous channels of the mesoporous fibrous silica, in comparison to silicas having micropores or silicas having mesopores that are not fibrous. Accordingly, the shell 20 of embodiments of the catalyst system 100 described herein can provide pre-cracking functionalities, which crack the bulky reactant molecules of crude oil and converted them into small molecules before entering into the micropores of the core 10 for further reaction.

In embodiments, at least a portion of the shell 20 may have a thickness of from 50 nanometers (nm) to 360 nm, from 50 nm to 350 nm, from 50 nm to 300 nm, from 50 nm to 250 nm, from 50 nm to 200 nm, from 50 nm to 150 nm, from 50 nm to 100 nm, from 50 nm to 90 nm, from 90 nanometers (nm) to 360 nm, from 90 nm to 350 nm, from 90 nm to 300 nm, from 90 nm to 250 nm, from 90 nm to 200 nm, from 90 nm to 150 nm, from 90 nm to 100 nm, from 100 nm to 360 nm, from 100 nm to 350 nm, from 100 nm to 300 nm, from 100 nm to 250 nm, from 100 nm to 200 nm, from 100 nm to 150 nm, from 150 nm to 360 nm, from 150 nm to 350 nm, from 150 nm to 300 nm, from 150 nm to 250 nm, from 150 nm to 200 nm, from 200 nm to 360 nm, from 200 nm to 350 nm, from 200 nm to 300 nm, from 200 nm to 250 nm, from 250 nm to 360 nm, from 250 nm to 350 nm, from 250 nm to 300 nm, from 300 nm to 360 nm, from 300 nm to 350 nm, or from 350 nm to 360 nm. Without being bound by theory, a greater shell thickness may allow for a shell 20 having improved thermal and mechanical stability. Furthermore, in embodiments, having a thicker shell may allow for increased pre-cracking functionalities, which subsequently allow for an improved overall yield of light olefins and other products.

In embodiments, the shell 20 may include heteroatoms, such as aluminum (Al), boron (B), and gallium (Ga); which are incorporated into the shell material. The heteroatoms may be incorporated into the mesoporous fibrous silica during the synthesis process, which increases the surface acidity of the shell 20 due to the formation of the Lewis and/or Bronsted acidic sites. Without being bound by theory, increasing the amount of acidic sites may increase the pre-cracking functionalities, which may improve the overall yield of light olefins and other products.

In one or more embodiments, the catalyst system 100 may further comprise one or more metallic nanoparticles supported on the shell 20. The one or more metallic nanoparticles may include nickel, cobalt, or platinum. Without being bound by theory, alumina incorporation may allow for pre-cracking functionalities to be imparted into the catalyst system, and metallic nanoparticle incorporation may allow for Sulphur and Nitrogen capturing functionalities to be imparted into the catalyst system. In embodiments, the catalyst system 100 may include up to 20 wt. % of the one or more metallic nanoparticles, based on the total weight of the catalyst system. In embodiments, the catalyst system 100 may include from 0.1 wt. % to 20 wt. %, from 0.1 wt. % to 15 wt. %, from 0.1 wt. % to 10 wt. %, from 0.1 wt. % to 5 wt. %, from 0.1 wt. % to 1 wt. %, from 1 wt. % to 20 wt. %, from 1 wt. % to 15 wt. %, from 1 wt. % to 10 wt. %, from 1 wt. % to 5 wt. %, from 5 wt. % to 20 wt. %, from 5 wt. % to 15 wt. %, from 5 wt. % to 10 wt. %, from 10 wt. % to 20 wt. %, from 10 wt. % to 15 wt. %, or from 15 wt. % to 20 wt. % of the one or more metallic nanoparticles, based on the total weight of the catalyst system.

The properties of the catalyst systems described herein may be tunable by controlling the synthesis parameters for producing the shell 20. The synthesis parameters may allow for precise control of one or more of the shell thickness, shell density, and surface acidity of the shell 20. In embodiments, parameters such as temperatures utilized during the synthesis procedure and the concentration of components may impact the catalyst system 100 formed. For example, the thickness and density of the shell 20 may be tunable by controlling synthesis parameters such as the amount of co-solvent or the manner by which the heteroatom is incorporated into the catalyst system 100.

Embodiments of producing the shell material include introducing the heteroatom into the shell material in situ. Introducing the heteroatom in situ may allow for a lower Si/Al molar ratio to be achieved in comparison to methods that incorporate the heteroatom by post-synthetic modification methods. To introduce the heteroatom in situ, an aluminum source may be utilized by a one-pot strategy. In embodiments, the aluminum source may be aluminum isopropoxide.

To produce the shell 20, cetyltrimethylammonium bromide (CTAB), urea, and, optionally, aluminum isopropoxide may be dissolved in deionized water to produce a first solution. In embodiments, the first solution may include from 0.1 wt. % to 5 wt. %, from 1 wt. % to 4 wt. %, or from 2 wt. % to 3 wt. % CTAB, based on the total weight of the first solution. Without being bound by theory, decreasing the amount of CTAB may increase the resultant shell thickness. In embodiments, the first solution may include from 0.1 wt. % to 5 wt. %, from 1 wt. % to 4 wt. %, or from 2 wt. % to 3 wt. % urea, based on the total weight of the first solution. In embodiments, the first solution may include from 0 wt. % to 5 wt.%, from 1 wt. % to 4 wt. %, or from 2 wt. % to 3 wt. % aluminum isopropoxide, based on the total weight of the first solution. In embodiments, the balance of first solution may be water. The first solution may be stirred under conditions sufficient to completely dissolve the cetyltrimethylammonium bromide. For example, the cetyltrimethylammonium bromide, urea, and aluminum isopropoxide may be stirred at a speed of from 500 rpm to 2000 rpm, from 500 rpm to 1500 rpm, from 500 rpm to 1000 rpm, from 1000 rpm to 2000 rpm, from 1000 rpm to 1500 rpm, or from 1500 rpm to 2000 rpm and from a time period of from 0.5 hours to 2 hours, from 0.5 hours to 1 hour, or from 1 hour to 2 hours to produce the first solution.

The first solution may then be sequentially added to a second solution comprising a solvent, such as cyclohexane, tetraethyl orthosilicate (TEOS), and a co-solvent, such as 1-pentanol. The second solution may include from 1 wt. % to 10 wt. %, from 1 wt. % to 8 wt. %, from 1 wt. % to 6 wt.

%, from 1 wt. % to 4 wt. %, from 1 wt. % to 2 wt. %, from 2 wt. % to 10 wt. %, from 2 wt. % to 8 wt. %, from 2 wt. % to 6 wt. %, from 2 wt. % to 4 wt. %, from 4 wt. % to 10 wt. %, from 4 wt. % to 8 wt. %, from 4 wt. % to 6 wt. %, from 6 wt. % to 10 wt. %, from 6 wt. % to 10 wt. %, from 6 wt. % to 8 wt. %, or from 8 wt. % to 10 wt. % of the co-solvent, based on the total weight of the second solution. The second solution may include from 0.5 wt. % to 10 wt. %, from 0.5 wt. % to 8 wt. %, from 0.5 wt. % to 6 wt. %, from 0.5 wt. % to 4 wt. %, from 0.5 wt. % to 2 wt. %, from 2 wt. % to 10 wt. %, from 2 wt. % to 8 wt. %, from 2 wt. % to 6 wt. %, from 2 wt. % to 4 wt. %, from 4 wt. % to 10 wt. %, from 4 wt. % to 8 wt. %, from 4 wt. % to 6 wt. %, from 6 wt. % to 10 wt. %, from 6 wt. % to 10 wt. %, from 6 wt. % to 8 wt. %, or from 8 wt. % to 10 wt. % of TEOS, based on the total weight of the second solution. In embodiments, the balance of second solution may be a hydrocarbon solvent, such as cyclohexane.

In embodiments, the TEOS/CTAB molar ratio, may be optimized to produce the core-shell structure of the catalyst system 100. In embodiments, the TEOS/CTAB molar ratio may be at least 10. Having a TEOS/CTAB molar ratio of less than 10 may not be sufficient to produce the core-shell structure. In further embodiments, the TEOS/CTAB molar ratio may be from 10 to 20, from 10 to 18, from 10 to 16, from 10 to 14, from 10 to 12, from 12 to 20, from 12 to 18, from 12 to 16, from 12 to 14, from 14 to 20, from 14 to 18, from 14 to 16, from 16 to 20, from 16 to 18, or from 18 to 20.

In embodiments, when the shell includes the heteroatom, Al, the shell 20 may have a Si/Al molar ratio of greater than 5. In embodiments, the shell 20 may have a Si/Al molar ratio of from 5 to 50 from 5 to 40, from 5 to 30, from 5 to 20, from 5 to 10, from 10 to 50, from 10 to 40, from 10 to 30, from 10 to 20, from 20 to 50, from 20 to 40, from 20 to 30, from 30 to 50, from 30 to 40, or from 40 to 50. Without being bound by theory, if the synthesis methods utilize an Si/Al molar ratio of less than 5, the catalyst produced may now have a core-shell structure. To produce a shell 20 having an Si/Al molar ratio of greater than 5, the molar ratio of the tetraethyl orthosilicate to aluminum isopropoxide may be greater than 5 or from 5 to 50 from 5 to 40, from 5 to 30, from 5 to 20, from 5 to 10, from 10 to 50, from 10 to 40, from 10 to 30, from 10 to 20, from 20 to 50, from 20 to 40, from 20 to 30, from 30 to 50, from 30 to 40, or from 40 to 50.

The resulting combination of the two solutions may then be stirred under conditions sufficient to mix the first and second solutions. For example, the first and second solutions may be stirred at room temperature at a speed of from 500 rpm to 2000 rpm, from 500 rpm to 1500 rpm, from 500 rpm to 1000 rpm, from 1000 rpm to 2000 rpm, from 1000 rpm to 1500 rpm, or from 1500 rpm to 2000 rpm and from a time period of from 0.5 hours to 3 hours, from 0.5 hours to 2 hours, from 0.5 hours to 1 hour, from 1 hours to 3 hours, from 1 hour to 2 hours, or from 2 hours to 3 hours to sufficiently mix the first solution and the second solution.

The mixture may then be transferred into an autoclave, such as a Teflon-lined steel autoclave. The mixture may be heated in the autoclave via a rotating oven.

The rotating oven may be heated at a ramping rate of from 1° C./minute to 10° C./minute, from 1° C./minute to 8° C./minute, from 1° C./minute to 6° C./minute, from 1° C./minute to 4° C./minute, from 1° C./minute to 2° C./minute, from 2° C./minute to 10° C./minute, from 2° C./minute to 8° C./minute, from 2° C./minute to 6° C./minute, from 2° C./minute to 4° C./minute, from 4° C./minute to 10° C./minute, from 4° C./minute to 8° C./minute, from 4° C./minute to 6° C./minute, from 6° C./minute to 10° C./minute, from 6° C./minute to 8° C./minute, or from 8° C./minute to 10° C./minute.

The rotating oven may be heated to a temperature of from 20° C. to 200° C., from 20° C. to 180° C., from 20° C. to 160° C., from 20° C. to 140° C., from 20° C. to 120° C., from 20° C. to 100° C., from 20° C. to 80° C., from 20° C. to 60° C., from 20° C. to 40° C., from 40° C. to 200° C., from 40° C. to 180° C., from 40° C. to 160° C., from 40° C. to 140° C., from 40° C. to 120° C., from 40° C. to 100° C., from 40° C. to 80° C., from 40° C. to 60° C., from 60° C. to 200° C., from 60° C. to 180° C., from 60° C. to 160° C., from 60° C. to 140° C., from 60° C. to 120° C., from 60° C. to 100° C., from 60° C. to 80° C., from 80° C. to 200° C., from 80° C. to 180° C., from 80° C. to 160° C., from 80° C. to 140° C., from 80° C. to 120° C., from 80° C. to 100° C., from 100° C. to 200° C., from 100° C. to 180° C., from 100° C. to 160° C., from 100° C. to 140° C., from 100° C. to 120° C., from 120° C. to 200° C., from 120° C. to 180° C., from 120° C. to 160° C., from 120° C. to 140° C., from 140° C. to 200° C., from 140° C. to 180° C., from 140° C. to 160° C., from 160° C. to 200° C., from 160° C. to 180° C., or from 180° C. to 200° C.

The mixture may be heated in the rotating oven for a time period of from 0.5 hours to 5 hours, from 0.5 hours to 4.5 hours, from 0.5 hours to 4 hours, from 0.5 hours to 3.5 hours, from 0.5 hours to 3 hours, from 0.5 hours to 2.5 hours, from 0.5 hours to 2 hours, from 0.5 hours to 1.5 hours, from 0.5 hours to 1 hour, from 1 hour to 5 hours, from 1 hour to 4.5 hours, from 1 hour to 4 hours, from 1 hour to 3.5 hours, from 1 hour to 3 hours, from 1 hour to 2.5 hours, from 1 hour to 2 hours, from 1 hour to 1.5 hours, from 1.5 hours to 5 hours, from 1.5 hours to 4.5 hours, from 1.5 hours to 4 hours, from 1.5 hours to 3.5 hours, from 1.5 hours to 3 hours, from 1.5 hours to 2.5 hours, from 1.5 hours to 2 hours, from 2 hours to 5 hours, from 2 hours to 4.5 hours, from 2 hours to 4 hours, from 2 hours to 3.5 hours, from 2 hours to 3 hours, from 2 hours to 2.5 hours, from 2.5 hours to 5 hours, from 2.5 hours to 4.5 hours, from 2.5 hours to 4 hours, from 2.5 hours to 3.5 hours, from 2.5 hours to 3 hours, from 3 hours to 5 hours, from 3 hours to 4.5 hours, from 3 hours to 4 hours, from 3 hours to 3.5 hours, from 3.5 hours to 5 hours, from 3.5 hours to 4.5 hours, from 3.5 hours to 4 hours, from 4 hours to 5 hours from 4 hours to 4.5 hours, or from 4.5 hours to 5 hours.

The rotating oven may operate at a speed of from 20 rpm to 100 rpm, from 20 rpm to 80 rpm, from 20 rpm to 60 rpm, from 20 rpm to 40 rpm, from 40 rpm to 100 rpm, from 40 rpm to 80 rpm, from 40 rpm to 60 rpm, from 60 rpm to 100 rpm, from 60 rpm to 80 rpm, or from 80 rpm to 100 rpm.

After heating in the rotating oven, solid product may be collected via centrifugation. The solid product may be washed. In embodiments, the solid product may be washed with water, acetone, or both. In embodiments, the solid product may be washed one or more times, for example, two times or three times.

The washed solid product may be dried in a convection oven for a temperature of from 50° C. to 150° C., from 50° C. to 125° C., from 50° C. to 100° C., from 50° C. to 75° C., from 75° C. to 150° C., from 75° C. to 125° C., from 75° C. to 100° C., from 100° C. to 150° C., from 100° C. to 125° C., or from 125° C. to 150° C. and at a time period of from 5 hours to 30 hours, from 5 hours to 25 hours, from 5 hours to 20 hours, from 5 hours to 15 hours, from 5 hours to 10 hours, from 10 hours to 30 hours, from 10 hours to 25 hours, from 10 hours to 20 hours, from 10 hours to 15 hours, from 15 hours to 30 hours, from 15 hours to 25 hours, from 15 hours to 20 hours, from 20 hours to 30 hours, from 20 hours to 25 hours, or from 25 hours to 30 hours.

Finally, to produce the catalyst system 100, the dried solid product may be calcined in air at a temperature of from 350° C. to 700° C., from 400° C. to 600° C., from 400° C. to 550° C., from 400° C. to 500° C., from 400° C. to 450° C., from 450° C. to 600° C., from 450° C. to 550° C., from 450° C. to 500° C., from 500° C. to 600° C., from 500° C. to 550° C., or from 550° C. to 600° C. for a time of from 2 hours to 10 hours, from 2 hours to 8 hours, from 2 hours to 6 hours, 2 hours to 4 hours, from 4 hours to 10 hours, from 4 hours to 8 hours, from 4 hours to 6 hours, from 6 hours to 10 hours, from 6 hours to 8 hours, or from 8 hours to 10 hours.

In embodiments, the catalyst system 100 may have a BET surface area, calculated by the Brunauer Emmett-Teller (BET) method of less than 700 m$^2$/g JMB. In further embodiments, the catalyst system 100 may have a BET surface area, calculated by the Brunauer Emmett-Teller (BET) method of from 400 m$^2$/g to 700 m$^2$/g, from 400 m$^2$/g to 600 m$^2$/g, from 400 m$^2$/g to 500 m$^2$/g, from 400 m$^2$/g to 480 m$^2$/g, from 400 m$^2$/g to 460 m$^2$/g, from 400 m$^2$/g to 440 m$^2$/g, from 400 m$^2$/g to 420 m$^2$/g, from 420 m$^2$/g to 500 m$^2$/g, from 420 m$^2$/g to 480 m$^2$/g, from 420 m$^2$/g to 460 m$^2$/g, from 420 m$^2$/g to 440 m$^2$/g, from 440 m$^2$/g to 500 m$^2$/g, from 440 m$^2$/g to 480 m$^2$/g, from 440 m$^2$/g to 460 m$^2$/g, from 460 m$^2$/g to 500 m$^2$/g, from 460 m$^2$/g to 480 m$^2$/g, from 480 m$^2$/g to 500 m$^2$/g, from 500 m$^2$/g to 700 m$^2$/g, from 500 m$^2$/g to 650 m$^2$/g, from 500 m$^2$/g to 600 m$^2$/g, from 550 m$^2$/g to 700 m$^2$/g, from 550 m$^2$/g to 650 m$^2$/g, from 550 m$^2$/g to 600 m$^2$/g, from 600 m$^2$/g to 700 m$^2$/g, or from 650 m$^2$/g to 700 m$^2$/g.

In embodiments, the catalyst system 100 may have a total relative pore volume, calculated by the Barrett, Joyner, and Halenda (BJH) method of less than 1.00 cm$^3$/g. In further embodiments, the catalyst system 100 may have a total relative pore volume, calculated by the Barrett, Joyner, and Halenda (BJH) method of from 0.10 cm$^3$/g to 1.00 cm$^3$/g, from 0.10 cm$^3$/g to 0.80 cm$^3$/g, from 0.10 cm$^3$/g to 0.60 cm$^3$/g, from 0.10 cm$^3$/g to 0.40 cm$^3$/g, from 0.10 cm$^3$/g to 0.20 cm$^3$/g, from 0.20 cm$^3$/g to 1.00 cm$^3$/g, from 0.20 cm$^3$/g to 0.80 cm$^3$/g, from 0.20 cm$^3$/g to 0.60 cm$^3$/g, from 0.20 cm$^3$/g, to 0.40 cm$^3$/g, from 0.40 cm$^3$/g to 1.00 cm$^3$/g, from 0.40 cm$^3$/g to 0.80 cm$^3$/g, from 0.40 cm$^3$/g to 0.60 cm$^3$/g, from 0.60 cm$^3$/g to 1.00 cm$^3$/g, from 0.60 cm$^3$/g to 0.80 cm$^3$/g, or from 0.80 cm$^3$/g to 1.00 cm$^3$/g.

In embodiments, the catalyst system 100 may have an overall Si/Al molar ratio of greater than 5. In embodiments, the catalyst system 100 may have an overall Si/Al molar ratio from 5 to 50, from 5 to 40, from 5 to 30, from 5 to 20, from 5 to 10, from 10 to 50, from 10 to 40, from 10 to 30, from 10 to 20, from 20 to 50, from 20 to 40, from 20 to 30, from 30 to 50, from 30 to 40, or from 40 to 50.

Methods of utilizing embodiments of the catalyst system 100 will now be described. In some embodiments, the catalyst system 100 may be utilized as a catalyst in a methanol to olefins process. In embodiments, the catalyst system 100 may be utilized as a catalyst in a one-step crude oil catalytic cracking process. In embodiments, the catalyst system 100 may be utilized in one or more steps of a hydrocracking process. In further embodiments, the one or more steps of the hydrocracking process may include hydrodenitrogenation, hydrodesulphurization, and hydrocracking steps that occur during a process of crude oil catalytic cracking to olefins and aromatics. In further embodiments, the catalyst system 100, and particularly the shell 20 of the catalyst system 100 may act as a catalytic support for metallic active sites, such as Co and Ni, which allow for improved capture and removal sulfur-containing—(e.g. dibenzothiophene) and nitrogen-containing (e.g. 2,6-dimethylpyridine) compounds by hydrogenation.

In one exemplary embodiment, a method for converting hydrocarbons may include contacting a feed with the catalyst system presently described. The catalyst system may comprise a core comprising a zeolite and a shell comprising a microporous fibrous silica, where the shell may be in direct contact with at least a majority of an outer surface of the core. The catalyst system may have a Si/Al molar ratio greater than 5. At least a portion of the shell may have a thickness of from 5 nm to 360 nm or from 50 nm to 360 nm. The shell may pre-crack the feed to produce a pre-cracked feed, and the core may crack the feed to produce light olefins. In embodiments, the feed may be crude oil.

Test Methods

Surface Area

The surface areas were calculated by the Brunauer Emmett-Teller (BET) method.

Pore Volume and Pore Diameter

The total relative pore volume and the average pore diameter were estimated from the amount of N2 adsorbed at P/P0=0.99 according to the Barrett, Joyner, and Halenda (BJH) method. (Barret E P, Joyner L J, Halenda P H, J. Am. Chem. Soc. 73 (1951) 373-380).

$N_2$ Physisorption,

Nitrogen physisorption measurements were performed at −196° C. on a Micromeritics ASAP 2460.

High-Angle Annular Dark-Field Scanning Transmission Electron Microscopy (HAADF-STEM)

HAADF-STEM is a STEM method where inelastically scattered electrons or thermal diffuse scattering (TDS) are received at high angles using an annular dark-field (ADF) detector (~50 to sufficiently high angle; e.g. ~200 mrad). A STEM image is acquired by displaying the integrated intensities of the electrons in synchronism with the incident probe position.

Ammonia Temperature Programmed Desorption ($NH_3$-TPD)

The $NH_3$-TPD was carried out on Micromeritics AutoChem II 2920. The solids are pretreated under He stream at 300° C. for 1 hour; then $NH_3$ (10 vol % $NH_3$ in He) is adsorbed at 50° C. for 1 hour; then the catalyst is purged by He until the baseline is stable; the TPD is then performed at with a ramp of 10° C./min.)

EXAMPLES

The following examples illustrate one or more additional features of the present disclosure. It should be understood that these examples are not intended to limit the scope of the disclosure or the appended claims in any manner.

In the following examples, the short b axis ZSM-5 was synthesized by adding 9.575 mL TPAOH (1 M), 5.975 mL TEOS, 1.0 g urea, 0.352 g Al(NO$_3$)$_3$.9H$_2$O, 0.05 g NaOH and 0.0636 mL IPA into 6.06 mL g H$_2$O under stirring. After stirring at room temperature for 1-2 h, the resulting solution was transferred into an autoclave for further crystallization. The autoclave was placed into a temperature programming oven. The oven was heated from room temperature to 180° C. with a rate of 25° C./h, and then held at 180° C. for 48 h. The obtained crystals were separated by filtration and washed by deionized water for three times, subsequently dried at 100° C. in air, then calcined at 550° C. for 5 h to remove the template. The obtained Na-ZSM-5 was converted to the ammonium form by cation-exchange in a $NH_4NO_3$ solution. 10 g Na-ZSM-5 was dispersed in 100 mL $NH_4NO_3$ solution (1 M) and vigorously stirred for 6 h. The exchange process was performed repeatedly for 3 times to complete the exchange reaction, and $NH_4$-ZSM-5 was formed. The HZSM-5 was obtained by calcining the $NH_4$-ZSM-5 powder at 550° C. for 5 h.

Example 1: Effect of TEOS/CTAB Ratio

In Example 1, three samples were prepared by combining and mixing cetyltrimethylammonium bromide, urea, and ZSM-5 in deionized water in the amounts according to Table 1. The resulting mixture was vigorously stirred at 1500 rpm for 1 hour until all the CTAB was completely dissolved and combined with a second solution of cyclohexane, tetraethyl orthosilicate (TEOS), and 1-pentanol in the amounts according to Table 1. The combined solutions were stirred at 1500 rpm for 3 hours at room temperature. Finally, this mixture was transferred into a Teflon-lined steel autoclave and heated at a ramping rate of 2.5° C./min to 120° C. for 4 hours in a rotating oven at 60 rpm. The resulting product was collected by centrifugation, washed with deionized water and acetone 3 times, dried in a convection oven 110° C. for 24 hours, and calcined in air at 550° C. for 6 hours.

Figure 2A:
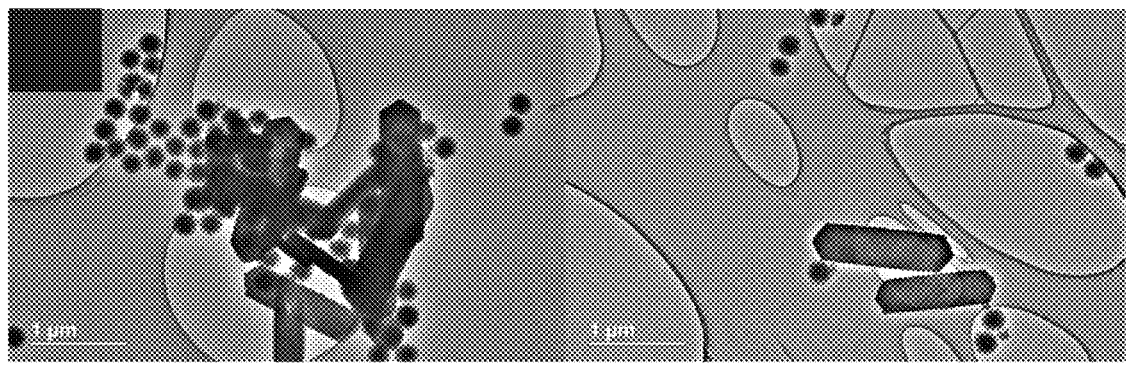
FIG. 2A is transmission electron microscopy (TEM) image of Comparative Sample A, having no core-shell morphology.
Figure 2B:
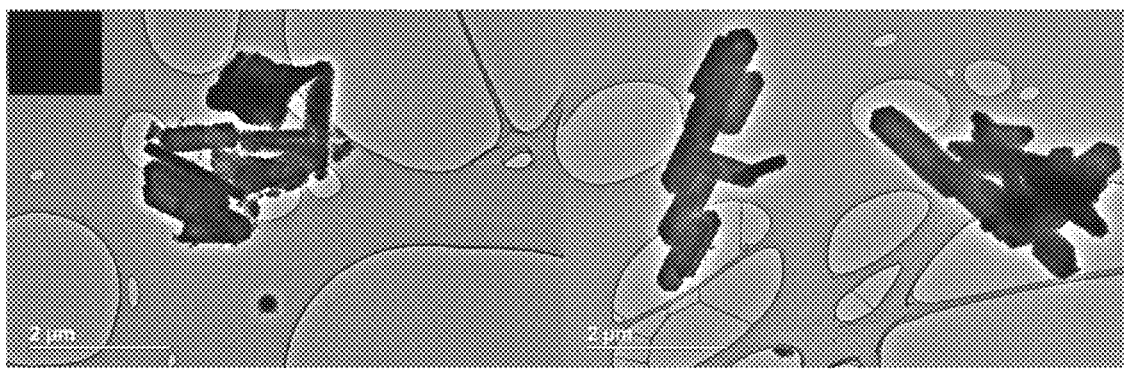
FIG. 2B is transmission electron microscopy (TEM) image of Comparative Sample B, having no core-shell morphology.
Figure 2C:
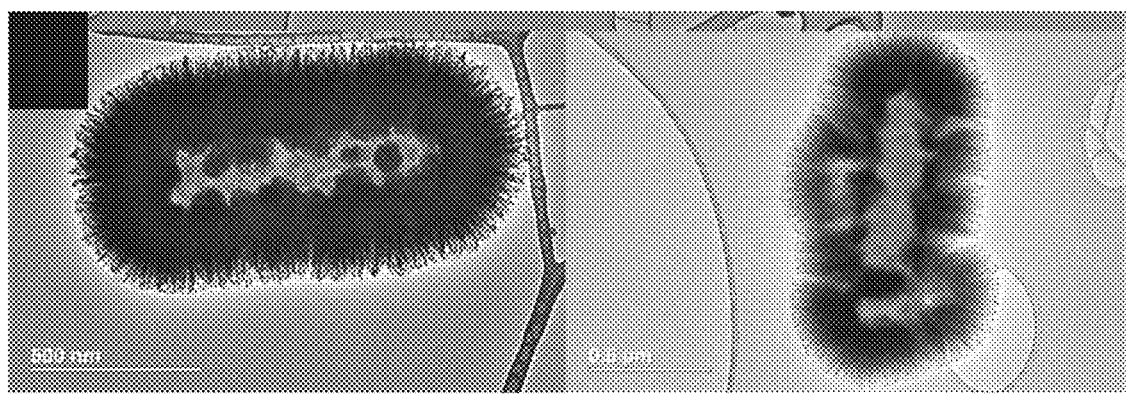
FIG. 2C is transmission electron microscopy (TEM) image of Sample 1, in accordance with one or more embodiments described herein.
Figure 3A:
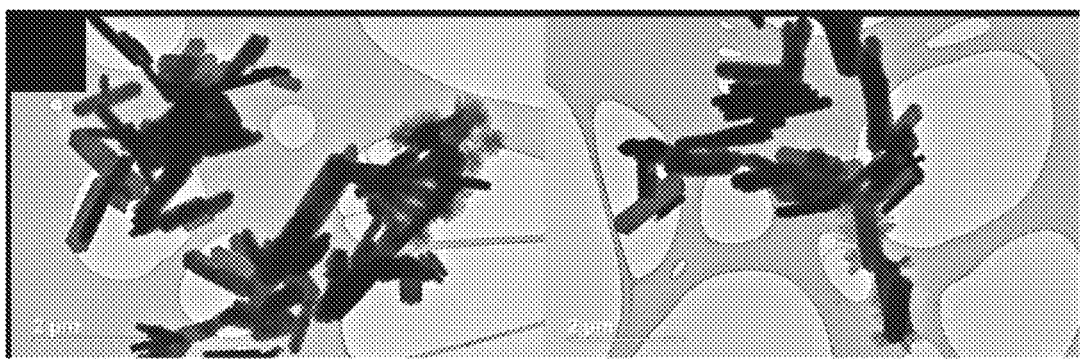
FIG. 3A is transmission electron microscopy (TEM) image of Comparative Sample C, having no core-shell morphology.
Figure 3B:
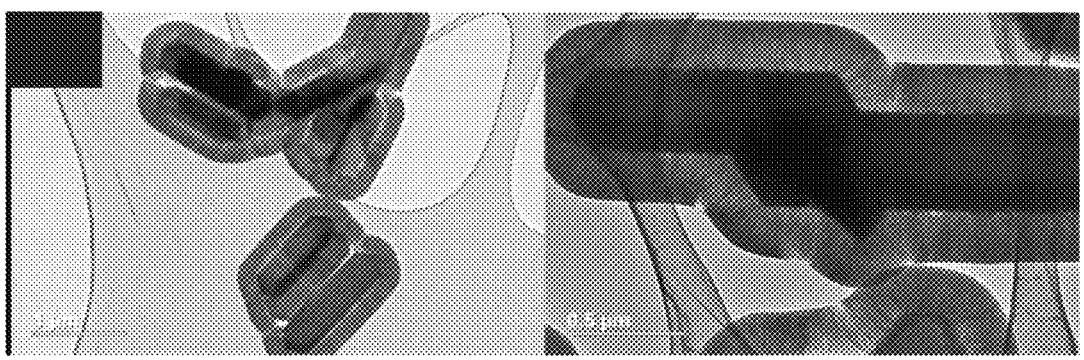
FIG. 3B is transmission electron microscopy (TEM) image of Sample 6, in accordance with one or more embodiments described herein.
Figure 3C:
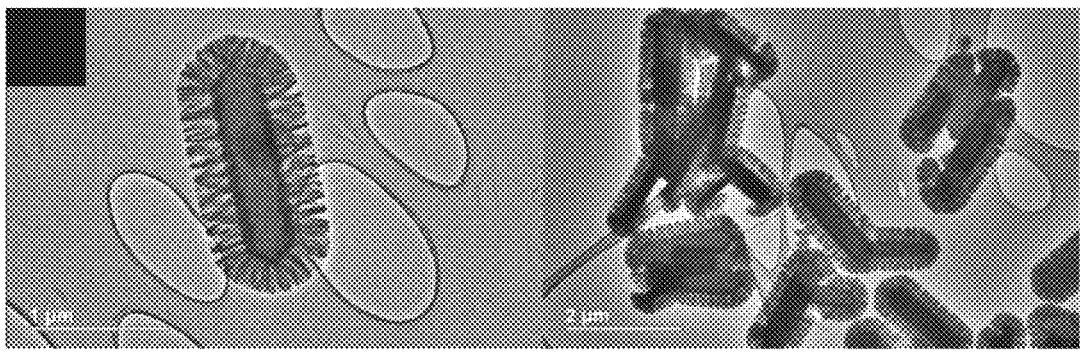
FIG. 3C is transmission electron microscopy (TEM) image of Sample 7, in accordance with one or more embodiments described herein.
Figure 3D:
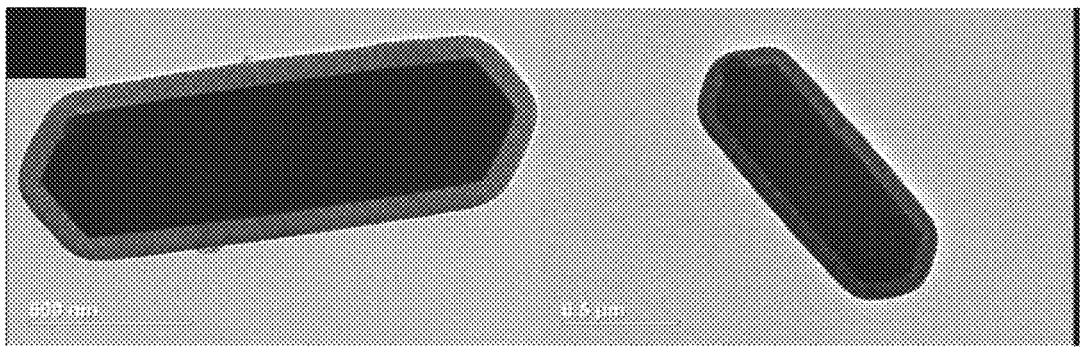
FIG. 3D is transmission electron microscopy (TEM) image of Sample 8, in accordance with one or more embodiments described herein.
Figure 4A:
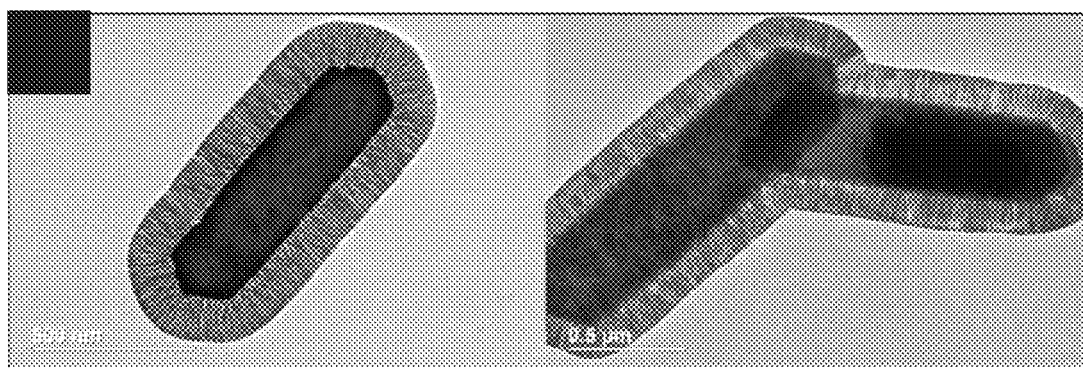
FIG. 4A is transmission electron microscopy (TEM) image of Sample 9, in accordance with one or more embodiments described herein.
Figure 4B:
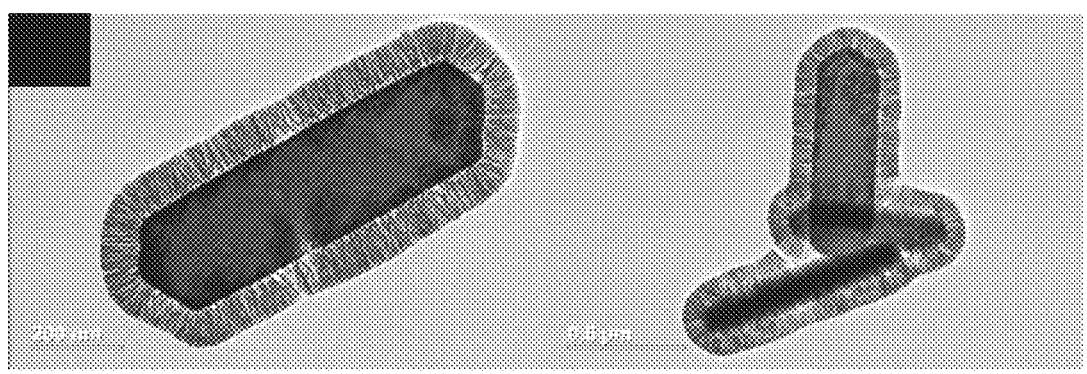
FIG. 4B is transmission electron microscopy (TEM) image of Sample 10, in accordance with one or more embodiments described herein.
Figure 4C:
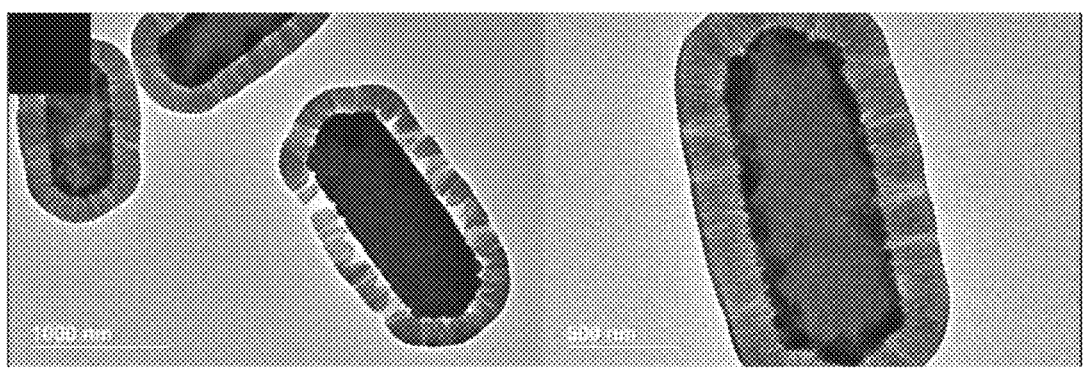
FIG. 4C is transmission electron microscopy (TEM) image of Sample 11, in accordance with one or more embodiments described herein.
Figure 4D:
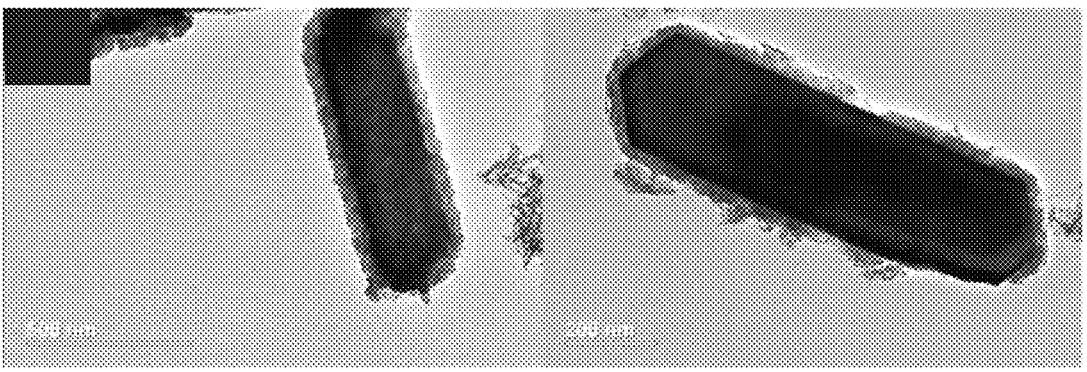
FIG. 4D is transmission electron microscopy (TEM) image of Comparative Sample D, having no fibrous shell.

The compositions of Comparative Sample A, Comparative Sample B, and Sample 1, each having different TEOS/CTAB ratios, are summarized in the Table 1. The TEM images associated with Comparative Sample A (FIG. 2A), Comparative Sample B (FIG. 2B), and Sample 1 (FIG. 2C) are each shown on FIG. 2.

TABLE 1

Effect of TEOS/CTAB.

|  | Comparative Sample A | Comparative Sample B | Sample 1 |
|---|---|---|---|
| TEOS/CTAB ratio | 4 | 8 | 16 |
| Water (mL) | 15 | 15 | 15 |
| Urea (mmol) | 3 | 3 | 3 |
| CTAB (mmol) | 1.5 | 0.75 | 0.375 |
| Cyclohexane (mL) | 15 | 15 | 15 |
| 1-pentanol (mL) | 0.75 | 0.75 | 0.75 |
| TEOS (mmol) | 6 | 6 | 6 |
| Zeolite (g) | 0.3648 | 0.3648 | 0.3648 |

As shown in FIG. 2, only Sample 1, having a TEOS/CTAB ratio of 16 possessed the core-shell structure. As a comparison, Comparative Sample A and Comparative Sample B, each with TEOS/CTAB ratios lower than 10 (4 and 8, respectively) did not show any core-shell structure.

Example 2: Effect of the Concentration of CTAB on the Shell Thickness

In Example 2, four samples were prepared by combining and mixing cetyltrimethylammonium bromide, urea, and ZSM-5 in deionized water in the amounts according to Table 2. The resulting mixture was vigorously stirred at 1500 rpm for 1 hour until all the CTAB was completely dissolved and combined with a second solution of cyclohexane, tetraethyl orthosilicate (TEOS), and 1-pentanol in the amounts according to Table 2. The combined solutions were stirred at 1500 rpm for 3 hours at room temperature. Finally, this mixture was transferred into a Teflon-lined steel autoclave and heated at a ramping rate of 2.5° C./min to 120° C. for 4 hours in a rotating oven at 60 rpm. The resulting product was collected by centrifugation, washed with deionized water and acetone 3 times, dried in a convection oven 110° C. for 24 hours, and calcined in air at 550° C. for 6 hours.

In order to investigate effect of the concentration of CTAB on the shell thickness, each composition had a TEOS/CTAB ratio of 16/1 and TEOS/urea ratio of 2/1, and the CTAB amount was 0.1875 mmol, 0.1250, 0.938, and 0.0750 for Samples 2, 3, 4, and 5, respectively.

TABLE 2

Effect of the concentration of CTAB on Shell Thickness.

|  | Sample 2 | Sample 3 | Sample 4 | Sample 5 |
|---|---|---|---|---|
| Water (mL) | 15 | 15 | 15 | 15 |
| Urea (mmol) | 1.5 | 1.0 | 0.75 | 0.60 |
| CTAB (mmol) | 0.1875 | 0.1250 | 0.938 | 0.0750 |
| Cyclohexane (mL) | 15 | 15 | 15 | 15 |
| 1-pentanol (mL) | 0.75 | 0.75 | 0.75 | 0.75 |
| TEOS (mmol) | 3 | 2 | 1.5 | 1.2 |
| ZSM-5 zeolite (g) | 0.1824 | 0.1216 | 0.0912 | 0.0730 |
| BET surface area ($m^2/g$) | 461.4 | 413.8 | 637.4 | 432.0 |
| BJH pore volume ($cm^3/g$) | 1.32 | 1.02 | 1.57 | 0.94 |
| Average pore diameter (nm) | 17.7 | 15.5 | 16.0 | 13.3 |
| Shell thickness (nm) | ~70 | ~80 | ~130 | ~260 |

As shown in Table 2, the shell thickness of the catalyst system gradually increased from 70 nm to 260 nm with the decrease of the CTAB amount from 0.1875 mmol to 0.0750 mmol.

Example 3: Effect of Co-solvent on Shell Thickness

In Example 3, four samples were prepared by combining and mixing cetyltrimethylammonium bromide, urea, and ZSM-5 in deionized water in the amounts according to Table 3. The resulting mixture was vigorously stirred at 1500 rpm for 1 hour until all the CTAB was completely dissolved and combined with a second solution of cyclohexane, tetraethyl orthosilicate (TEOS), and 1-pentanol in the amounts according to Table 3. The combined solutions were stirred at 1500 rpm for 3 hours at room temperature. Finally, this mixture was transferred into a Teflon-lined steel autoclave and heated at a ramping rate of 2.5° C./min to 120° C. for 4 hours in a rotating oven at 60 rpm. The resulting product was collected by centrifugation, washed with deionized water and acetone 3 times, dried in a convection oven 110° C. for 24 hours, and calcined in air at 550° C. for 6 hours. As shown in Table 3, in Example 3, the amount of 1-pentanol was varied to observe its effect on the formation and the thickness of the KCC-1 shell.

TABLE 3

Effect of Co-solvent on Shell Thickness.

|  | Comparative Sample C | Sample 6 | Sample 7 | Sample 8 |
|---|---|---|---|---|
| Water (mL) | 15 | 15 | 15 | 15 |
| Urea (mmol) | 0.60 | 0.60 | 0.60 | 0.60 |
| CTAB (mmol) | 0.0750 | 0.0750 | 0.0750 | 0.0750 |
| Cyclohexane (mL) | 15 | 15 | 15 | 15 |
| 1-pentanol (mL) | 0.00 | 0.375 | 0.75 | 1.50 |
| TEOS (mmol) | 1.2 | 1.2 | 1.2 | 1.2 |
| ZSM-5 zeolite (g) | 0.0730 | 0.0730 | 0.0730 | 0.0730 |
| BET surface area ($m^2/g$) | 428.8 | 451.7 | 432.0 | 439.3 |

TABLE 3-continued

Effect of Co-solvent on Shell Thickness.

| | Comparative Sample C | Sample 6 | Sample 7 | Sample 8 |
|---|---|---|---|---|
| BJH pore volume (cm³/g) | 0.50 | 0.69 | 0.94 | 0.56 |
| Average pore diameter (nm) | 6.35 | 8.56 | 13.3 | 8.33 |
| Shell thickness (nm) | No core-shell | ~220 | ~360 | ~80 |

FIG. 3 shows the TEM images of Comparative Sample C (FIG. 3A), Sample 6 (FIG. 3B), Sample 7 (FIG. 3C), and Sample 8 (FIG. 3D) synthesized with different amounts of 1-pentanol co-solvent. As shown in FIG. 3, it was clearly observed in FIG. 3A, Comparative Sample C had no core-shell structure and was observed as compared to FIGS. 3B, 3C, and 3D, which showed that Sample 6, Sample 7, and Sample 8 each had a core-shell structure. Therefore, these results showed the role of the co-solvent in the formation of the shell structure. Furthermore, the thickness of the shell was affected by the amount of the co-solvent, as shown in FIGS. 3B, 3C, and 3D.

Example 4: Effect of Si/Al Molar Ratio

In Example 4, four samples were prepared by combining and mixing cetyltrimethylammonium bromide, urea, aluminum isopropoxide, and ZSM-5 in deionized water in the amounts according to Table 4. The resulting mixture was vigorously stirred at 1500 rpm for 1 hour until all the CTAB was completely dissolved and combined with a second solution of cyclohexane, tetraethyl orthosilicate (TEOS), and 1-pentanol in the amounts according to Table 3. The combined solutions were stirred at 1500 rpm for 3 hours at room temperature. Finally, this mixture was transferred into a Teflon-lined steel autoclave and heated at a ramping rate of 2.5° C./min to 120° C. for 4 hours in a rotating oven at 60 rpm. The resulting product was collected by centrifugation, washed with deionized water and acetone 3 times, dried in a convection oven 110° C. for 24 hours, and calcined in air at 550° C. for 6 hours. As shown in Table 4, in Example 4, the Si/Al molar ratio was varied to observe its effect on the catalyst system.

TABLE 4

Effect of Si/Al Molar Ratio of Shell.

| | Sample 9 | Sample 10 | Sample 11 | Comparative Sample D |
|---|---|---|---|---|
| Si/Al molar ratio of Shell | ∞ | 40 | 20 | 5 |
| Water (mL) | 30 | 30 | 30 | 30 |
| Urea (mmol) | 1.2 | 1.2 | 1.2 | 1.2 |
| CTAB (mmol) | 0.150 | 0.150 | 0.150 | 0.150 |
| Cyclohexane (mL) | 30 | 30 | 30 | 30 |
| 1-pentanol (mL) | 0.75 | 0.75 | 0.75 | 0.75 |
| TEOS (mmol) | 2.4 | 2.4 | 2.4 | 2.4 |
| ZSM-5 zeolite (g) | 0.1460 | 0.1460 | 0.1460 | 0.1460 |
| Aluminum isopropoxide (g) | 0 | 0.0122 | 0.0244 | 0.0980 |
| Shell thickness (nm) | 140 nm | 90 nm | 180 nm | No fibrous KCC-1 |

As shown in Table 4 and FIG. 4, the core-shell structure of the catalyst system could be successfully retained with the decrease of the Si/Al molar ratio from ∞ to 20. See Sample 9 (FIG. 4A), Sample 10 (FIG. 4B), and Sample 11 (FIG. 4C). However, further decreasing the Si/Al molar ratio to 5, as shown with Comparative Sample D (FIG. 4D), the morphology of the shell failed to be fibrous and failed to entirely surround the surface area of the core, although a portion of the core-shell structure was still retained.

Figure 5:
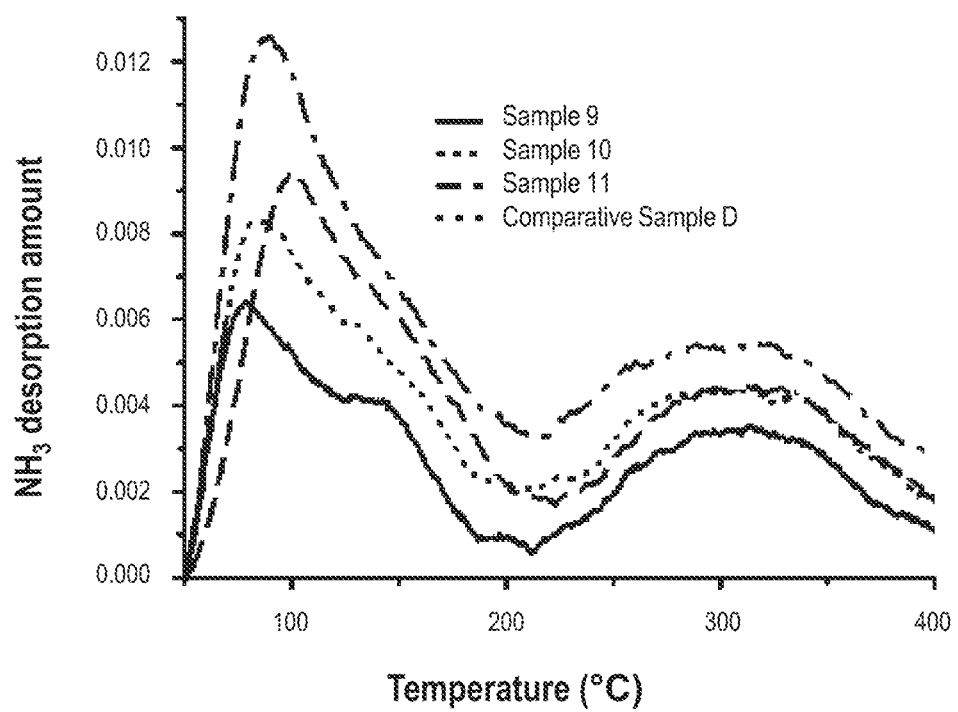
FIG. 5 depicts a comparison of the $NH_3$-TPD profiles of Sample 9, Sample 10, Sample 11, and Comparative Sample D.

The $NH_3$-TPD had been carried out to investigate the effect of the Si/Al molar ratio of the Al-KCC-1 shell on the acidity of the catalyst systems, and the resultant profiles of Comparative Sample C, Sample 6, Sample 7, and Sample 8 are summarized in FIG. 5. As shown in FIG. 5A, as the Si/Al molar ratio decreased from ∞ to 5, the intensities of the $NH_3$-TPD profiles gradually increased. This indicated that the acidity of the core-shell could be increased by lowering the Si/Al molar ratio.

Figure 6:
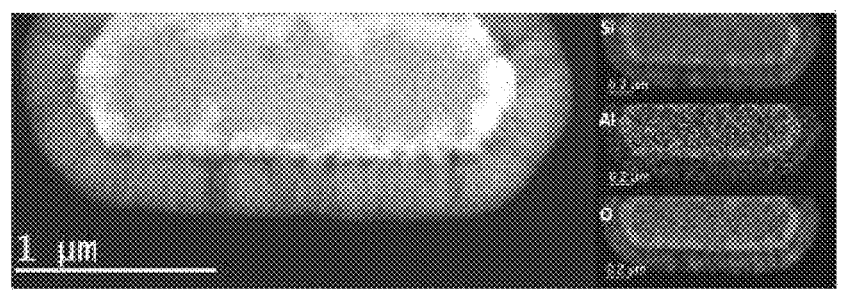
FIG. 6 is a HAADF-STEM element-mapping image of Sample 11, in accordance with one or more embodiments described herein.
Figure 7:
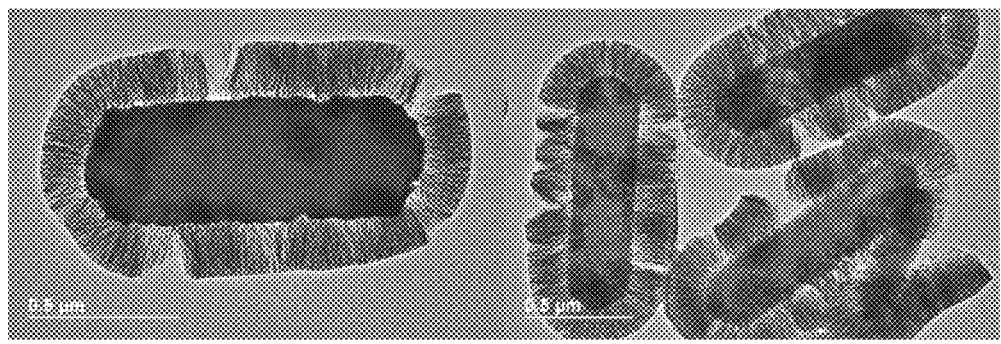
FIG. 7 is transmission electron microscopy (TEM) image of Sample 12, in accordance with one or more embodiments described herein.
Figure 8:
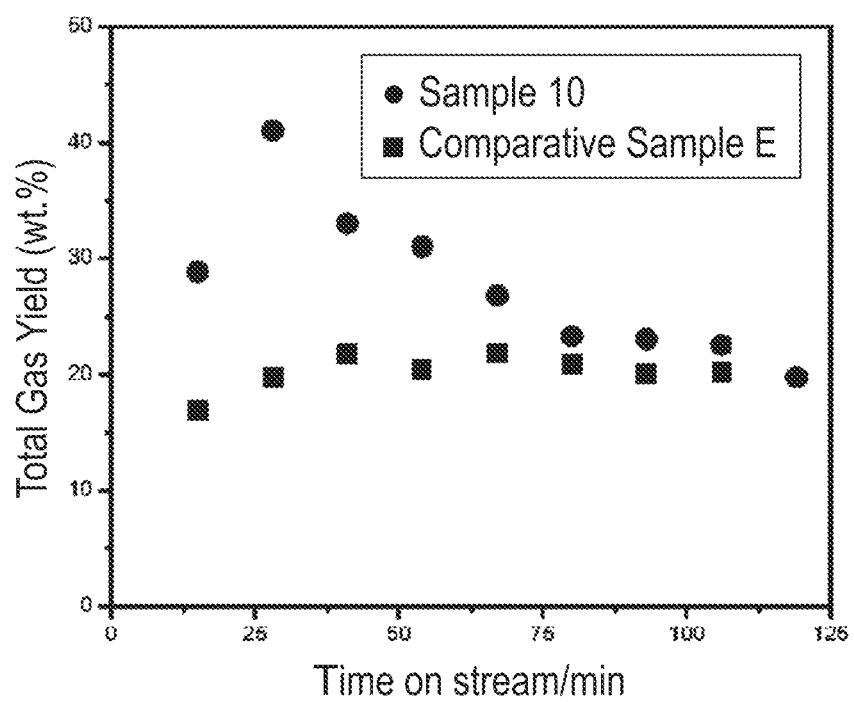
FIG. 8 graphically depicts the total gas yield for Sample 10 and Comparative Sample E when utilized in Example 8.
Figure 9:
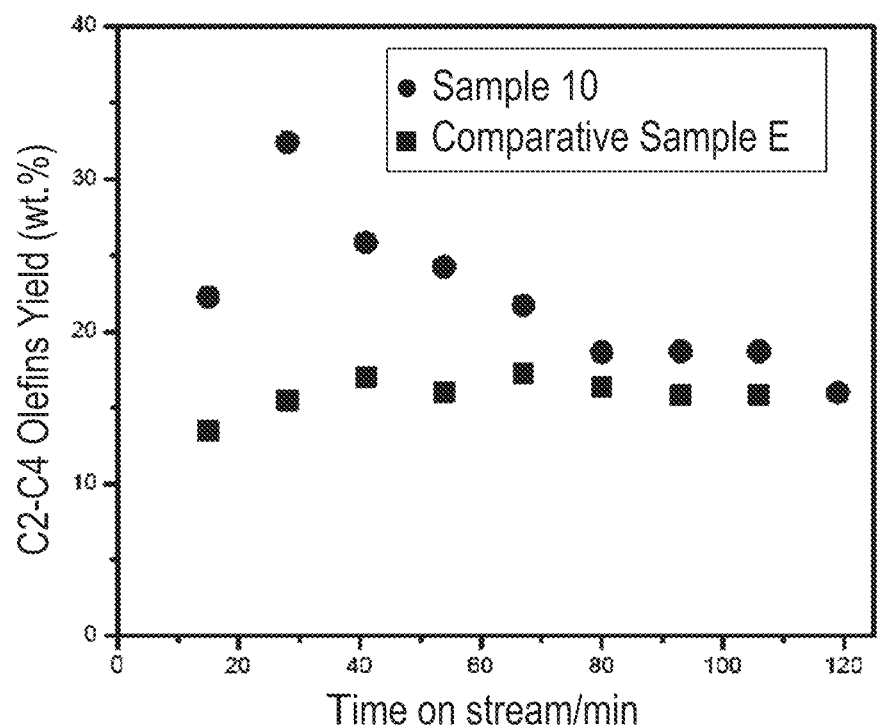
FIG. 9 graphically depicts the C2-C4 olefins yield for Sample 10 and Comparative Sample E when utilized in Example 8.
Figure 10:
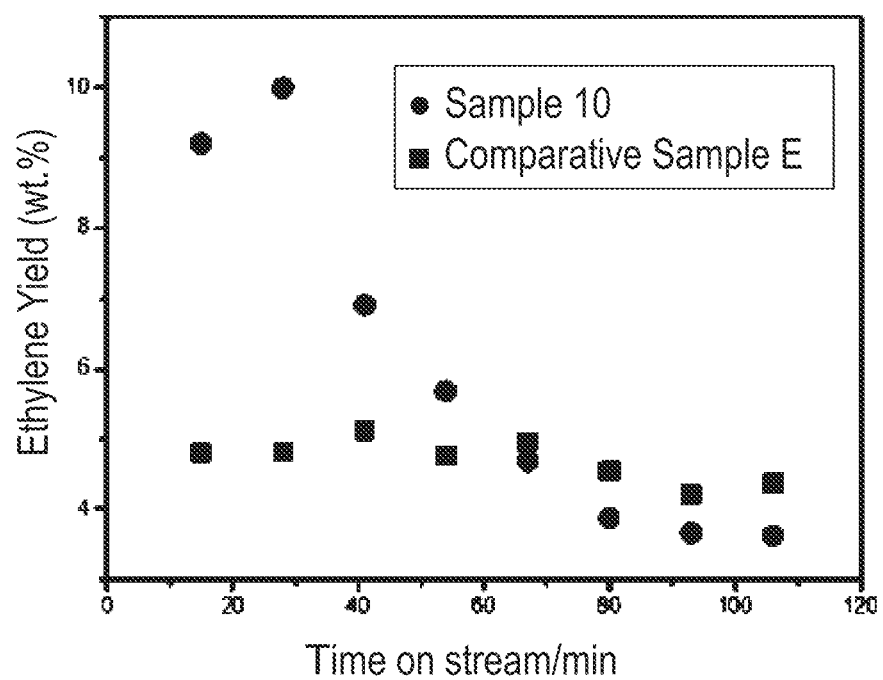
FIG. 10 graphically depicts the ethylene yield for Sample 10 and Comparative Sample E when utilized in Example 8.
Figure 11:
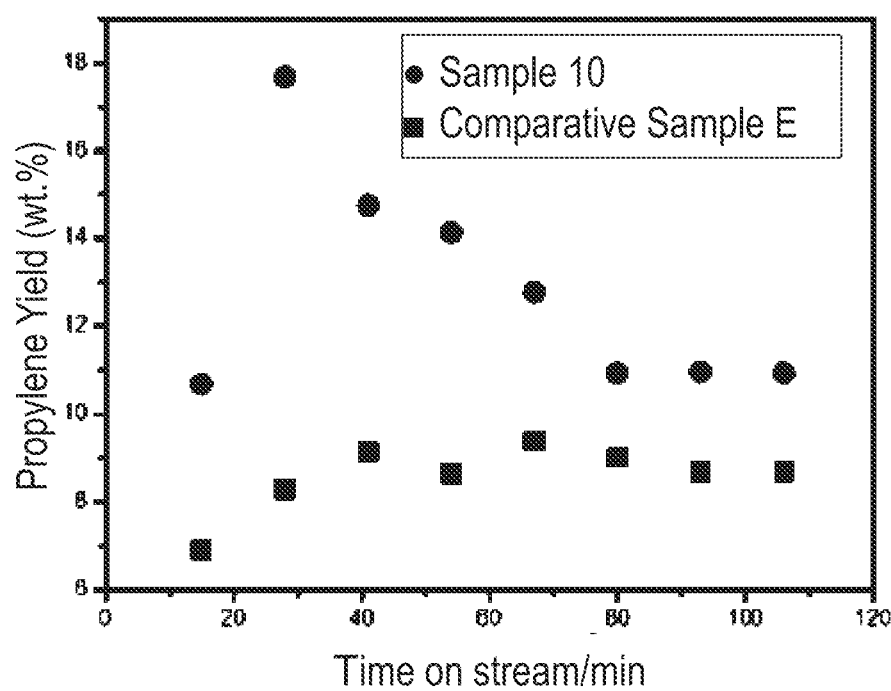
FIG. 11 graphically depicts the propylene yield for Sample 10 and Comparative Sample E when utilized in Example 8.
Figure 12:
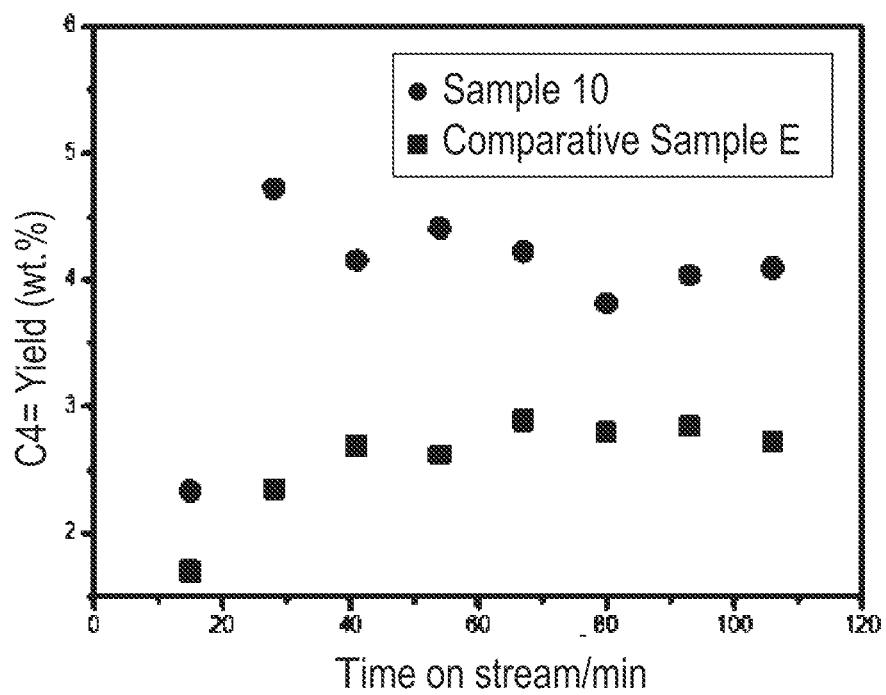
FIG. 12 graphically depicts the C4=yield for Sample 10 and Comparative Sample E when utilized in Example 8.

For Sample 11, HAADF-STEM element-mapping characterization was carried out for Sample 11 in order to confirm the spatial distribution of the aluminum in the Al-KCC-1 shell. As shown in FIG. 6, the Si, Al, and O were homogenously distributed among the core and shell. This suggested that the aluminum had been successfully incorporated into the shell without destroying the fibrous KCC-1 morphology.

Example 5: Comparison of ZSM-5 (Comparative Sample E), ZSM-5/KCC-1 (Sample 9), and ZSM-5/Al-KCC-1 (Sample 10)

In Example 5, $N_2$ physisorption analyses were carried out for catalyst systems comprising ZSM-5 only (Comparative Sample E), ZSM-5 and KCC-1 (Sample 9), and ZSM-5 and Al-KCC-1 (Sample 10).

Comparative Sample E comprised ZSM-5 only and had an Si/Al ratio of 40. Sample 9 had a ZSM-5 core with an Si/Al ratio of 40 and a KCC-1 shell having no aluminum incorporated into the shell. Sample 10 had a ZSM-5 core with an Si/Al ratio of 40 and a Al-KCC-1 shell with an Si/Al ratio of 40.

TABLE 5

Structural properties of Comparative Sample E, Sample 9, and Sample 10.

| | Comparative Sample E | Sample 9 | Sample 10 |
|---|---|---|---|
| Morphology | ZSM-5 core with Si/Al = 40 | ZSM core with Si/Al = 40 and KCC-1 shell (with no Al) | ZSM-5 core with Si/Al = 40 and Al-KCC-1 shell with Si/Al = 40 |
| BET surface area (m²/g) | 366.5 | 481.4 | 476.2 |
| BJH pore volume (cm³/g) | 0.091 | 0.714 | 8.17 |
| Average pore diameter (nm) | 3.99 | 8.17 | 8.97 |

As shown in Table 5, Sample 9 and Sample 10 possessed the additional mesoporous structure (larger BET surface area, larger pore volume, and larger pore diameter) compared to Comparative Sample D.

Example 6: Scaled-up Synthesis

In Example 6, a scaled-up synthesis procedure was utilized to synthesize a catalyst system (Sample 12) having a Si/Al molar ratio of 40. For the specific procedure of the scale-up synthesis, a solution of 4.100 g cetyltrimethylammonium bromide (CTAB), 5.40 g urea, 0.919 g aluminum isopropoxide, and 10.90 g ZSM-5 were mixed in 2.250 mL deionized water at 1500 rpm for 1 hour until all the CTAB was completely dissolved. After that, the first solution was sequentially added to a second solution of 2.250 mL cyclohexane, 39.9 mL tetraethyl orthosilicate (TEOS), and 56.25 mL 1-pentanol. The first solution and second solution were stirred at room temperature and 1500 rpm for 3 hours. Finally, this mixture was transferred into a 20 L steel autoclave and heated at a ramping rate of 2.5° C/minute to a temperature of 120° C. in an rotating oven 60 rpm for four hours. The resulting product was collected by centrifugation, washed with deionized water and acetone for 3 times, dried in a convection oven at 110° C. for 24 hours, and calcined in air at 550° C. for 6 hours.

As shown in FIG. 6, the core-shell structure could be clearly observed.

Example 7: Evaluation of the Catalytic Performance—Methanol to Olefins

In Example 7, catalyst systems according to embodiments disclosed herein were investigated as the catalysts for methanol-to-olefins processes. The methanol to olefins process was carried out under the following specific conditions: 500° C., 50 mg catalyst, WHSV=10 $h^{-1}$, 1 bar.

TABLE 6

Methanol-to-Olefins Results for Comparative Sample E and Sample 10 after 14 hours.

|  | Comparative Sample E ZSM-5 only (Si/Al = 40) | Sample 10 ZSM-5 and Al-KCC-1 (Si/Al = 40) |
|---|---|---|
| Methanol conversion (%) | 100 | 100 |
| Dimethyl ether selectivity (%) | 0 | 0 |
| C2-C4 selectivity (%) | 41 | 55 |
| C2-C4 alkanes selectivity (%) | 28 | 15 |
| Aromatics selectivity (%) | 21 | 18 |
| Methane ($CH_4$) selectivity (%) | 6.5 | 7 |

As shown in Table 6, the methanol conversion was retained at 100% during the whole 14 hour test for both samples. Additionally, after 14 hours the dimethyl ether selectivity over these two catalysts was almost 0% (and during the whole 14 h time on stream), suggesting the strong acidity of both catalysts because the formation of dimethyl ether usually occurs on the weak acidic sites. Moreover, Sample 10 showed a higher selectivity of olefins compared to Comparative Sample E, and Comparative Sample E had a higher selectivity of C2-C4 alkanes in comparison to Sample 10. Additionally, the selectivity of aromatics and methane were both similar over both Comparative Sample E and Sample 10.

Example 8: Evaluation of the Catalytic Performance—Crude Oil Catalytic Cracking In Example 8, catalyst systems according to embodiments disclosed herein were investigated as the catalysts for crude oil catalytically cracking processes.

The evaluation of the crude oil (Arabian Light) catalytic cracking was carried out on a fixed bed reactor at a temperature of 570° C. with 50 mg catalyst and a liquid feed (comprised of 0.05 mL/min Arabian Light and 0.05 mL/min $H_2O$) and a 100 mL/min gas feed.

As shown in FIGS. 8 through 12, Sample 10 displayed a higher Total Gas Yield and C2-C4 Olefins Yield than Comparative Example E, which suggests that the pre-cracking functionalities of the Al-KCC-1 shell of Sample 10 contributed to improved catalytic performance. As for the specific yields of the olefins products, Sample 10 having the Al-KCC-1 shell also displayed higher ethylene yield, propylene yield, and C4=olefins yield than Comparative Sample E.

From these results, it may be apparent that utilizing the disclosed catalyst systems, having a zeolite core and a microporous fibrous silica shell optionally comprising a heteroatom, would boost the conversion, propylene yield, or selectivity compared to catalyst systems comprising only a ZSM-5 zeolite.

It should be understood that any two quantitative values assigned to a property may constitute a range of that property, and all combinations of ranges formed from all stated quantitative values of a given property are contemplated in this disclosure. It should be appreciated that compositional ranges of a chemical constituent in a composition or formulation should be appreciated as containing, in some embodiments, a mixture of isomers of that constituent. It should be appreciated that the examples supply compositional ranges for various compositions, and that the total amount of isomers of a particular chemical composition can constitute a range.

It is noted that one or more of the following claims utilize the term "where" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Rather, the claims appended hereto should be taken as the sole representation of the breadth of the present disclosure and the corresponding scope of the various embodiments described in this disclosure. Further, it should be apparent to those skilled in the art that various modifications and variations can be made to the described embodiments without departing from the spirit and scope of the claimed subject matter. Thus it is intended that the specification cover the modifications and variations of the various described embodiments provided such modifications and variations come within the scope of the appended claims and their equivalents.

What is claimed is:

1. A catalyst system comprising:
    a core comprising a ZSM-5zeolite;
    a shell comprising a mesoporous fibrous silica comprising KCC-1 and heteroatoms comprising aluminum, the shell in direct contact with at least a majority of an outer surface of the core; and
    wherein:
        the catalyst system has a Si/Al molar ratio of greater than 5 to equal or less than 20, and
        at least a portion of the shell has a thickness of from 90 nanometers (nm) to 180 nm.
2. The catalyst system of claim 1, wherein the shell is in direct contact with and surrounds the core.

3. The catalyst system of claim 1, wherein the heteroatoms further comprises boron, gallium, or both.

4. The catalyst system of claim 1, wherein at least a portion of the shell has a Brunauer-Emmett-Teller (BET) surface area of from 370 m² g to 650 m²/g.

5. The catalyst system of claim 1, wherein at least a portion of the shell has a Barrett, Joyner and Halenda (BJH) pore volume from 0.1 cm³ g to 1.0 cm³/g.

6. The catalyst system of claim 1, wherein at least a portion of the shell has an average pore diameter between 4 nm to 20 nm.

7. The catalyst system of claim 1, wherein:
the ZSM-5 zeolite has a Si/Al molar ratio of from 12 to 20; and
the shell has a Si/Al molar ratio of from 5 to 20.

8. The catalyst system of claim 1, wherein:
the KCC-1 is formed from a solution comprising cetyltrimethylammonium bromide, urea, tetraethyl orthosilicate, a hydrocarbon solvent comprising cyclohexane, and a co-solvent comprising 1-pentanol; and
the heteroatoms are formed from an aluminum source comprising aluminum isopropoxide, the aluminum source also being a part of the solution.

9. A method of synthesizing a catalyst system having a core-shell morphology, the method comprising:
mixing cetyltrimethylammonium bromide, urea, aluminum isopropoxide, a zeolite, and water to produce a first solution;
mixing a hydrocarbon solvent, tetraethyl orthosilicate, and a co-solvent to produce a second solution;
mixing the first solution and the second solution to produce a mixture; and
heating the mixture to produce the catalyst system, wherein the catalyst system comprises:
a core comprising a ZSM-5 zeolite;
a shell comprising a mesoprous fibrous silica comprising KCC-1 and heteroatoms comprising aluminum, the shell in direct contact with at least a majority of an outer surface of the core; and
wherein:
the catalyst system has a Si/Al molar ratio of greater than 5 to equal or less than 20, and
at least a portion of the shell has a thickness of from 90 nanometers (nm) to 180 nm.

10. The method of claim 9, wherein a molar ratio of the tetraethyl orthosilicate to cetyltrimethylammonium bromide is greater than 10.

11. The method of claim 9, wherein a molar ratio of the tetraethyl orthosilicate to aluminum isopropoxide is from 5 to 20.

12. The method of claim 9, further comprising washing and calcining the heated mixture.

13. The method of claim 9, wherein the co-solvent is 1-pentanol.

14. The method of claim 9, wherein the second solution comprises from 1 wt. % to 10 wt. % of the co-solvent, based on the total weight of the second solution.

15. A method for converting hydrocarbons, the method comprising contacting a feed with a catalyst system, the catalyst system comprising:
a core comprising a ZSM-5 zeolite;
a shell comprising a mesoporous fibrous silica comprising KCC-1 and a heteroatom comprising aluminum, the shell in direct contact with at least a majority of an outer surface of the core; and
wherein:
the catalyst system has a Si/Al molar ratio of greater than 5 to equal or less than 20;
at least a portion of the shell has a thickness of from 90 nanometers (nm) to 180 nm;
the shell pre-cracks the feed to produce a pre-cracked feed; and
the core cracks the pre-cracked feed to produce light olefins.

16. The method of claim 15, wherein the feed comprises crude oil.

* * * * *

UNITED STATES PATENT AND TRADEMARK OFFICE
CERTIFICATE OF CORRECTION

| | |
|---|---|
| PATENT NO. | : 11,938,466 B2 |
| APPLICATION NO. | : 17/315886 |
| DATED | : March 26, 2024 |
| INVENTOR(S) | : Xu et al. |

Page 1 of 1

It is certified that error appears in the above-identified patent and that said Letters Patent is hereby corrected as shown below:

In the Claims

Claim 14, Column 18, Line 18, "on the total weight..." should read --on a total weight...--

Signed and Sealed this
Fourteenth Day of May, 2024

Katherine Kelly Vidal
*Director of the United States Patent and Trademark Office*